United States Patent [19]
Schlipalius

[11] Patent Number: 5,612,485
[45] Date of Patent: Mar. 18, 1997

[54] HIGH CIS BETA-CAROTENE COMPOSITION

[75] Inventor: Lance E. Schlipalius, Ashwood, Australia

[73] Assignee: Betatene Ltd of Cheltenham, Victoria, Australia

[21] Appl. No.: 347,458

[22] PCT Filed: Jun. 4, 1993

[86] PCT No.: PCT/AU93/00267

§ 371 Date: Dec. 5, 1994

§ 102(e) Date: Dec. 5, 1994

[87] PCT Pub. No.: WO93/24454

PCT Pub. Date: Dec. 9, 1993

[30] Foreign Application Priority Data

Jun. 4, 1992 [AU] Australia .................................. PL2789

[51] Int. Cl.$^6$ .......................... C07C 403/00; C07C 7/20; C10M 105/02
[52] U.S. Cl. .................................. 585/351; 585/1; 585/3
[58] Field of Search ..................................... 585/1, 3, 351

[56] References Cited

U.S. PATENT DOCUMENTS

| | | | |
|---|---|---|---|
| 3,039,877 | 6/1962 | Borenstein | 99/81 |
| 3,367,985 | 2/1968 | Surmatis | 260/666 |
| 3,441,623 | 4/1969 | Surmatis | 260/666 |
| 3,492,202 | 1/1970 | Bohinski | 195/28 |
| 3,989,757 | 11/1976 | Surmatis | 260/598 |
| 4,199,895 | 4/1980 | Avron et al. | 47/1.4 |
| 4,439,629 | 3/1984 | Rüegg | 585/803 |
| 4,713,398 | 12/1987 | Nonomura | 514/725 |
| 4,851,339 | 7/1989 | Hills | 435/67 |
| 5,019,668 | 5/1991 | Keat et al. | 585/864 |
| 5,206,025 | 4/1993 | Courteille et al. | 424/439 |
| 5,245,095 | 9/1993 | Graves et al. | 585/351 |
| 5,310,554 | 5/1994 | Haigh | 424/439 |
| 5,382,732 | 1/1995 | Frank et al. | 585/351 |
| 5,453,447 | 9/1995 | Evod et al. | 585/351 |

OTHER PUBLICATIONS

Ami Ben–Amotz et al., *Stereoisomers of β–Carotene and Phytoene in the Alga Dunaliella Bardawil*, 86 Plant Physiol. 1286 (1988).

Ami Ben–Amotz & Mordhay Avron, *The Wavelength Dependence of Massive Carotene Synthesis in Dunaliella Bardawill (Chlorophyceae)*, 25 J. Phycol. 175 (1989).

Ami Ben–Amotz et al., *Bioavailability of a Natural Isomer Mixture as Compared with Synthetic all–trans–βCarotene in Rats and Chicks*, 119 J. Nutr. 1013 (1989).

O. Isler, ed. *Carotenoids*, Birk häuser Verlag, Basel, 1971, pp. 195, 198, 236, 237, 239, 251, 268–275, 281, 284–287, 328, 474–482, 489, 545, 682, 761.

T. Movinobu et al., "Changes in β–Carotene Levels by Long–Term Administration of Natural β–Carotene Derived from *Dunaliella bardawil* in Humans", J. Nutri. Sci. Vitamind., vol. 90, pp. 421–430, 1994.

R. Bushvay, "Separation of Carotenoids in Fruits and Vegetables by High Performance Liquid Chromatography", J. Liquid Chromatography, vol. 8, No. 8, pp. 1527–1547, 1985.

F. Quackenbush, "Reverse Phase HPLC Separation of CIS–and Trans–Carotenoids And its Application To βCarotenes in Food Materials", J. Liquid Chromatography, vol. 10, No. 4, pp. 643–653, 1987.

J. Bieri et al., "Determination of Individual Carotenoids in Human Plasma by High Performance Liquid Chromatography", J. Liquid Chromatography, vol. 8, No. 3, pp. 473–484, 1985.

(List continued on next page.)

*Primary Examiner*—Asok Pal
*Assistant Examiner*—J. Pasterczyk
*Attorney, Agent, or Firm*—Burns, Doane, Swecker & Mathis LLP

[57] ABSTRACT

A carotenoid composition derived from a natural source wherein at least 50% by weight of the carotenoid content of the composition is cis beta-carotene and preferably 9 cis beta-carotene. Typically, the beta-carotene content of the composition is predominantly 9 cis beta-carotene.

19 Claims, 1 Drawing Sheet

OTHER PUBLICATIONS

B. Borenstein et al., "Carotenoids: Properties, Occurrence, and Utilization in Foods", Food Res., vol. 15, pp. 195–276, 1966.

A. Ben–Amotz et al., "Photosynthetic Activities of the Halophilic Alga *Dunaliella parva*", Plant Physiol., vol. 49, No. 2, pp. 240–244, 1972.

R. Evans et al., "Lipid composition of halophilic species of *Dunaliella* from the dead sea", Archives of Microbiology, vol. 140, pp. 50–56, 1984.

A. Ben–Amotz et al., "Accumulation of β–carotene in halotolerant algae: purification and characterization of β–carotene–rich globules from *Dunaliella bardawil* (Chlorophyceae)", J. Phycol., pp. 529–537, 1982.

A. Shaish et al., "Effect of Inhibitors on the Formation of Stereoisomers in the Biosynthesis of β–Carotene in *Dunaliella bardawil*", Plant Cell Physiol., vol. 31, No. 5, pp. 689–696, 1990.

A. Ben–Amotz, et al., "Use of the β–carotene rich alga *Dunaliella bardawil* as a source of retinol", British Poultry Science, vol. 27, pp. 613–619, 1986.

A. Gillam et al., "The Isomerization of Carotenes by Chromatographic Adsorption. II.Neo–α–Carotene", Biochem. J., vol. 31, pp. 1605–1610, 1937.

L. Zechmeister et al., "Isomerization of Carotenoids", Biochem. J., vol. 32, pp. 1305–1311, 1938.

A. Gillam et al., "The Isomerization of Carotenes by Chromatographic Adsorption. I. Pseudoα–Carotene", Biochem. J., vol. 30, pp. 1735–1742, 1936.

D. M. Snodderly et al., "Plasma Carotenoids of Monkeys (*Macaca fascicularis and Saimiri sciureus*) Fed a Nonpurified Diet", J. Nutr., vol. 120, pp. 1663–1671, 1990.

C. Jensen et al., "Observations on the Effects of Ingesting CIS–and trans–beta–carotene Isomers on Human Serum Concentrations", Nutrition Reports International, vol. 35, No. 2, pp. 413–422, 1987.

H. Nagasawa, et al., "Inhibition by Beta–Carotene—Rich Algae *Dunaliella* of Spontaneous Mammary Tumourigenesis in Mice", Anticancer Research, vol. 9, pp. 71–76, 1989.

HIGH CIS BETA-CAROTENE COMPOSITION

FIELD OF THE INVENTION

The invention relates to a carotenoid composition derived from a natural source, with a high cis beta-carotene concentration and its preparation from natural sources, and more preferably a high 9 cis beta-carotene composition and its preparation from natural sources.

BACKGROUND OF THE INVENTION

In this specification it is to be understood that the natural sources of carotene include fruits, vegetables and other plant tissue, and animal tissue. A particularly important commercial source of carotene is certain types of algae.

Beta-carotene occurs in a number of different chemical isomer forms. Some of these are geometrical isomers which have a different orientation around one of the double bonds in the conjugated double bond structure of the molecule.

This can occur in a number of positions along the conjugated backbone to make a range of different geometrical isomers. In some cases there can even be more than one double bond where change of orientation occurs.

The most common geometrical isomer is the all trans isomer with a structure occurring as shown as follows where the main carbon chain of the molecule occurs in a trans (across) or straight configuration.

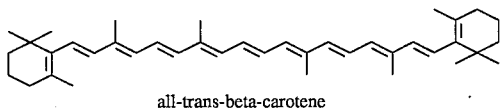

all-trans-beta-carotene

However, there are cis forms of beta-carotene which occur naturally, and can be produced by chemical synthesis, or formed by physical processes like heat on the all trans isomers, where the main carbon chain of the molecule takes a bend (cis) or sideways configuration. Naturally occurring cis forms of beta-carotene are not known to occur over a weight percentage of approximately 30% to less than 50% of the total carotenoid content.

Associated with the different geometric isomers are different properties and possible functions and for this reason there are potential benefits in relatively concentrated forms of the cis isomers.

In natural products such as fruit, vegetables, algae and other plant and animal material the carotenoids are stabilized as part of the cell structure in small micron or sub-micron sized particles in the cell organelles or even by association with other molecules which stabilize the isomeric forms produced by the biochemical pathways of the organism. However, in the preparation of concentrated forms of these materials for commercial products desired from the natural sources, the natural stabilising capacity of the cellular structure may be removed or reduced in the extraction and concentration of the carotenoids.

In addition, as the carotenoid products are concentrated to increase their beta-carotene concentrations and to remove the other cell material which is not desired in the product, there is a natural tendency for certain isomers to crystallize out.

Crystallisation is a problem in certain applications since the crystalline form may not be available for efficient use in the application because of its relative insolubility. Crystallisation occurs particularly with all trans beta-carotene and as a result it is not, for example, readily available for biological use.

Cis isomers, on the other hand are much less likely to crystallise and as a consequence are much more soluble than the trans isomers. For this reason, it is often more desirable to use beta-carotene containing compositions with higher concentrations of cis isomers for various applications. For example, the 9 cis isomer is much more readily soluble in oils than the all trans form. In fact, it is very difficult to get the 9 cis isomer to crystallize out from naturally derived oils, thus making it difficult or expensive to purify on a large scale.

Unlike trans isomers, cis isomers have a number of applications, including use in water dispersible food colourants and in tabletting powders. The cis isomers are also useful in a water dispersible form as emulsions for colouring and in beverages. They can also be used in special vitamin supplements in concentrates for direct supplementation or as part of food.

In naturally occurring products the proportion of cis isomers is rather small, but one of the highest proportions occurs in the halophillic alga *Dunaliella salina* where normally 30% to below 50% of the total carotenoid content occurs as the 9 cis form.

The present invention is accordingly directed to compositions with a high cis beta-carotene composition derived from natural sources.

DESCRIPTION OF THE INVENTION

Figure 1:
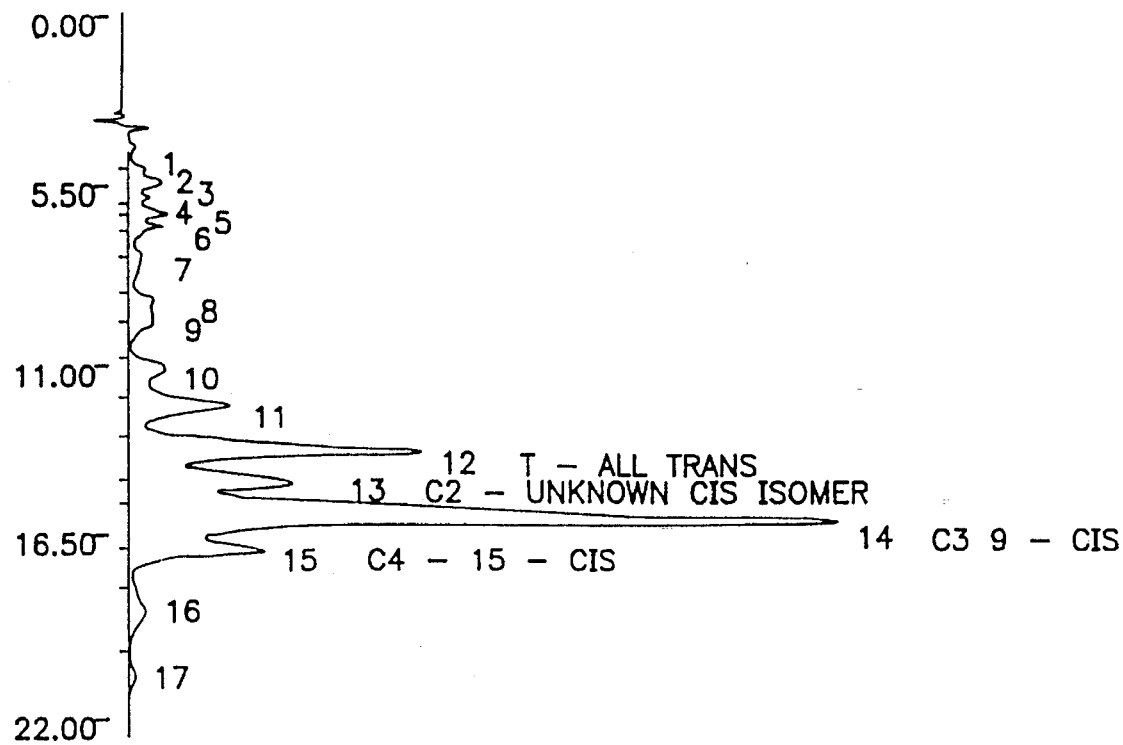
FIG. 1 illustrates a sample chromatogram displaying the isomeric analysis of a carotenoid composition as described in the Examples.

Accordingly, in one form of this invention, a carotenoid composition derived from a natural source is produced, wherein at least 50% by weight of the carotenoid content of the composition is cis beta-carotene and preferably 9 cis beta-carotene. Typically, the beta-carotene content is predominantly 9 cis beta-carotene.

In another form of the invention, the preferred range of cis beta-carotene is between at least 50% and 80%, and more preferably between 60% and 70%. Another preferred range is between 60% and 85%.

In yet another preferred form of the invention, the high cis beta-carotene from natural sources is derived (for example, by concentration and purification by physical means) from a product of lower concentrations of the cis beta-carotene to a concentration of at least 70% cis beta-carotene. Preferably this may be achieved by the removal of the substantially all trans beta-carotene using physical processes.

These high percentage cis isomer compositions have been found to exhibit high solubility and are readily available for physiologically active purposes. This is thought to be because of the following factors in particular:

(a) cis isomers occur in human body tissues in significant amounts and since the action of metabolism occurs in the tissues it is possible that the cis isomers have a physiological function;

(b) cis isomers are typically lower in the bloodstream which is higher in the all trans isomer; this suggests the cis isomers may be rapidly taken into the tissues; and (c) cis isomers appear to be easily absorbed from the intestine.

For example, high percentage cis isomers would be expected to have improved effect in use in medical applications, for example, in the healing and prevention of cancer, cardiovascular disease and other illnesses, since the cis isomers, because of their solubility, are likely to preferentially accumulate in the tissues being removed from the bloodstream over the trans form.

The improved solubility is also likely to assist in the application of the high percentage cis isomer in the topical application of the composition and for ease in the preparation in food colour applications. The cis isomers may assist in the stability of emulsions or powders of beta-carotene for commercial purposes which is partly due to their solubility characteristics.

The structure of the 9 cis isomer of beta-carotene is as follows:

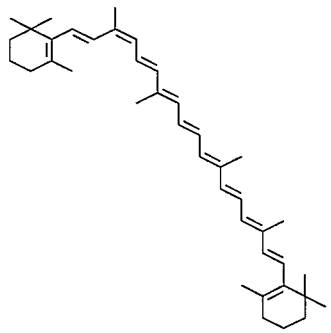

9-cis-beta-carotene

This 9 cis isomer of beta-carotene is preferably derived from particular natural sources of plant products including green peppers, apricots, flowers of certain species of the Acacia genus, *cucurbitaceae* and in the alga, *Dunaliella salina*, which has the highest concentration of the 9 cis isomer of such sources. In this regard, see Ami Ben-Amotz, Amnon Lers and Mordhay Aron: "Steroisomers of Beta-Carotene and Phytoene in the Alga *Dunaliella bardawil*" Plant Physiol. (1988) 86, 1286–1291 (*Dunaliella bardawil* has subsequently been acknowledged by Ami Ben-Amotz as naturally occurring *Dunaliella salina*).

The proportion of the total cis isomers (predominantly the 9 cis isomer) content in the total carotenoid content of the alga *Dunaliella salina* is normally found at around 30% to below 50% of the total carotenoid content on a weight basis as determined by the high pressure liquid chromatography (see method below commencing at page 14) and visible light spectrophotometry techniques.

Preferably, the increase of the 9 cis isomers in the composition is to about 70% of the total carotenoid absorbance and more preferably 80% of the total carotenoid content. The remaining 20% typically would consist of all trans beta-carotene (for example 10%), other cis forms (for example 5%) and other carotenoids (for example 5%).

The finished product is preferably dispersed in a natural carrier oil from animal, vegetable and mineral origins and particularly olive, corn, soya bean, essential oils, terpene based oils and fish derived oils.

The provisions of small quantities of oil soluble anti-oxidants may be beneficial for certain applications of the product. Examples of these would be butylated hydroxy anisole, butylated hydroxytoluene, propyl gallate, ethoxyquin and ascorbyl palmitate plus other natural antioxidant extracts, for example, derived from herbs and preferably natural tocopherols.

The anti-oxidants may be used to assist to protect the high cis beta-carotene preparations from oxidation, which is relatively more important when in a lower total beta-carotene concentration product, for example, less than 5% of beta-carotene in the preparation. However, even at higher concentrations it is important to protect the beta-carotene preparations from oxidising.

A concentration of 0.01% to 1.0%, preferably 0.01% to 0.5%, of the pure active anti-oxidant is typically used, depending on the actual anti-oxidant of choice and application, as this concentration range has been shown by experience to be sufficient for normal protection of the ultimate composition over its shelf life.

EXAMPLES OF METHODS TO PRODUCE THE HIGH CIS ISOMER COMPOSITION

The product is prepared by a series of physical unit operations. Examples of methods used to produce high cis isomer compositions, and more preferably to produce high 9 cis isomers are set out below as Example A and Example B.

Example A demonstrates a method using centrifugation (which relies on the principle of separation by density difference). The crystalline fraction containing the trans crystal is separated from the cis isomer soluble oil fraction.

This type of separation can either be done in a batch type centrifuge, usually on a small scale or for laboratory use or in a continuous machine to process larger volumes on an industrial scale.

The density of the all trans isomer crystals is greater than the cis isomers (including the 9 cis isomer) when in solution in vegetable oils having a relative density of about 0.92 grams per cubic centimeter. When the temperature or melting point of the carrier vegetable oil permits the oil to be liquid and of a viscosity to allow the all trans crystals to settle when the centrifugal force is applied, centrifugation will separate the all-trans isomer from the cis isomers. Being of the greater density, the all trans crystals can be separated by sedimentation and leave the machine in the heavy fraction and the cis isomers stay in the soluble vegetable oil or light fraction.

Centrifuges (for example, an Alfa Laval model number FUVPX207) which are capable of opening the bowl to remove a semi solid heavy sludge can concentrate the all trans crystals in this sludge thus increasing the yield of the high cis light fraction. The flow rate of material through the centrifuge has a large bearing on the result so this has to be optimized for the machine concerned.

Example B relies on filtration using a basket type centrifuge and filter bag, however, it will be readily understood by a person skilled in the art that the filtering operation can be performed on a range of filter materials, including a filter press, drum filter, filter beds, filter cartridge systems and more sophisticated membrane type filters. Any filter system can be used that employs pads, paper, cartridge filters or a centrifugal filtration using a filter in a basket centrifuge.

The crystals of all trans beta-carotene are held by the filter material but the soluble all cis material can pass through the filter thus increasing the proportion of cis isomers in the filtrate, that is, the product passing through the filter material.

Example A.

Ten grams of 4% natural beta-carotene in soya bean oil (commercially available from Betatene Limited and sold under the brand name "Betatene Limited 4% Natural Beta-Carotene in Soya Bean Oil") was placed in an 18 mm diameter glass centrifuge tube and centrifuged at 2000 revolutions per minute for 15 minutes at 21° C. in a Clements 2000 laboratory centrifuge.

At the conclusion, the supernatant oil (the light fraction) was recovered by removal with a Pasteur pipette and assayed for cis and trans beta-carotene content. After draining the residual supernatant from the heavy fraction, the same analysis was performed on the pelleted heavy fraction.

The percentages of the cis (including the 9 cis) beta-carotene and all trans beta-carotene (determined using the the high pressure liquid chromatography method commencing on page 14) were as follows:

|  | CIS total predominantly 9 cis % of total carotenoid by weight | All TRANS |
|---|---|---|
| Original 4% | 42 | 45 |
| Light fraction | 62 | 24 |
| Heavy fraction | 19 | 74 | with the crystals being collected in the heavy phase or the sludge fraction and the high cis product as the light fraction. The residue includes other carotenoids.

The same procedure can be performed on a continuous production scale using an open bowl desludging centrifuge such as an Alfa Laval model number FUVPX 207. The flow rate of the feed to the centrifuge, the setting of the skimmer to recover the high cis light fraction and the desludging timing would need to be optimised for the machine or other similar machines. This will be well understood by persons skilled in the art.

Example B.

A crystalline suspension of beta-carotene in soya bean oil containing 21% total carotenoid was filtered to retain crystals and to allow the soluble fraction to pass through. The all trans crystals can be separated from an oil based matrix, providing the oil is not too viscous to restrict movement of the oil through the filter bed. The starting material is available from Betatene Limited and is sold under the brand name "Betatene Limited 20% Natural Beta-Carotene in Soya Bean Oil".

This operation can be achieved in a basket type centrifuge of a type like a Broadbent, Tolhurst for Burton with a 900 mm diameter bowl, or a similar machine. The bowl is made of perforated stainless steel plate and a fabric bag is placed in the bowl with a weave having gaps between the fibres of approximately 20 to 25 microns in width. The 20% natural beta-carotene in soya bean oil is fed into the bag and the high trans crystals are retained on the bag letting the soluble high cis fraction pass through the bag and the perforations in the bowl. In the initial stages the filtrate may still contain the smaller crystals but this is overcome by recirculation through the centrifuge. Before long the crystal bed on the inner surface of the bag acts as the main filter which will remove the small crystals. The operation continues till the flow of filtrate through the bag is too slow. The filtrate is collected as are the retained crystals at the end of the run and analysed for beta-carotene and cis-trans isomeric profile.

The percentages of the cis beta-carotene and all trans beta-carotene (determined using the using the the high pressure liquid chromatography method commencing on page 14) were as follows:

|  | CIS predominantly 9 cis % of total carotenoid by weight | TRANS |
|---|---|---|
| Initial 21% oil suspension | 32 | 63 |
| Filtrate | 82 | 14 |
| Filtered crystals | 27 | 68 |

The residue includes other carotenoids.

Example A is an actual example of a method that has been carried out on a laboratory scale. Example B was carried out on a production scale.

It would also be understood by persons skilled in the art that cis isomers could be separated on a larger scale using preparative high pressure liquid chromatography. For example, *Dunaliella salina* algae which has a 9 cis isomer content of below 50% could be treated by preparative high pressure liquid chromatography techniques to separate the isomers and obtain a very high purity product of the 9 cis isomer (for example, 80% or more of the 9 cis isomer). This separation technique relies on the variable retention of different chemical materials to a solid phase when the materials in various mixtures of volatile organic solvents are pumped through the solid phase, usually in the form of spheres in a column. By collecting fractions at the end of the column the chemical materials may be separated from each other. The volatile organic solvents are evaporated from the pure chemical to provide the solvent free product.

EXAMPLE OF ISOMERIC ANALYSIS OF A CAROTENOID COMPOSITION USING HIGH PRESSURE LIQUID CHROMOTOGRAPHY

The following is an example of a standard method for conducting an isomeric analysis of a carotenoid composition using high pressure liquid chromatography to determine the percentage content of the cis isomers of beta-carotene and all trans beta-carotene. This was the method used in analysing the isomeric percentages in Example A and Example B above.

In summary, a sample of a beta-carotene containing composition in oil is dissolved in cyclohexene and diluted to a suitable concentration. Before injecting the resultant solution into the high pressure liquid chromatograph, the sample should be diluted with a mobile phase. The concentration of beta-carotene is determined by obtaining an absorbance at a specific wavelength using a known extinction coefficient. The cis and trans contents are determined by separating the isomers by high pressure liquid chromatography. The percentages of cis isomers and trans isomers are then determined as a percentage of the total carotenoid content.

(i) Reagents and Equipment

The following is a list of the reagents and equipment that can be used in the analysis.
Spectrophotometer with 10 mm glass cells
Analytical balance
Cyclohexane AR grade
100 ml volumetric flasks
50 ml volumetric flasks
2.0 ml bulb pipettes
Chloroform AR grade High pressure liquid chromatograph incorporating:
Isocratic pump
Injector able to handle up to 50 μl
UV/Vis detector set at 453 nm Vydac 201TP54 reverse phase column 250 mm Acetonitrile HPLC grade
Methanol HPLC grade
10 ml volumetric flask (ii) Preparation of the mobile phase Prior to the analysis being conducted, a mobile phase should be prepared by weighing 400 g of acetonitrile into a 1000 ml storage bottle, adding 300 g methanol and mixing well. The resultant mixture should be adjusted to room temperature before being used in the analysis.

(iii) Procedure

The method used in the actual analysis is set out below.

A sample of beta-carotene in oil is weighed accurately (to within 0.01 g) to the equivalent to 80 mg of beta-carotene into a 100 ml volumetric flask. Approximately 5 ml of chloroform is added and mixed well until the sample has dissolved. To ensure that the sample has completely dissolved it should be viewed against a light source. If the sample is not completely dissolved, it should be allowed to stand for approximately 5 minutes. It is also possible to add a further 5 ml of chloroform and to warm the mixture under, for example, hot tap water.

The volume of the mixture is then diluted with cyclohexane and mixed well. This is solution A. 2 ml of solution A is then pipetted into a 50 ml volumetric flask and diluted to volume with cyclohexane and mixed well. This is solution B. 2 ml of solution B is then pipetted into a 50 ml volumetric flask and diluted to volume with cyclohexane and mixed well. This is solution C. The absorbance of solution C is then measured at 455 nm against a cyclohexene blank (this gives the total beta-carotene content and not the isomeric ratio). 1 ml of solution B is then pipetted into a 10 ml volumetric flask, diluted to volume with the carrier solvent and mixed well. This is solution D.

(iv) Standards

For comparative purposes, a standard is then prepared. The standard is prepared to provide a reference material of known concentration in the assay and to determine reference retention time ("R.T.") for the all trans isomer. The standard is made up according to the same procedure used to make up the sample. Weigh the reference standard material (Sigma all trans beta-carotene from Sigma Corporate in St Louis USA) to the equivalent of 80 mg of beta-carotene, then proceed as for the sample. The concentration of the standard is determined in the same way as the sample.

(v) Determination

The standard and the sample as prepared above are ready for injection.

The flow rate of the high pressure liquid chromatograph should be set to 1.0 ml/minute, 20 μl of the standard is injected into the high pressure liquid chromatograph and allowed to run for 25 minutes. The injection concentration and volume are recorded. 20 μl of solution D is then injected into the high pressure liquid chromatograph and allowed to run for 25 minutes. The injection concentration and volume are recorded.

An example of a typical chromatogram is reproduced in FIG. 1.

(vi) Calculation

I—Calculation for Determination of Beta-carotene Concentration

The bracketed figures are typical figures.

| Absorbance of solution C at 455 nm | Abs | (−0.4) |
|---|---|---|
| Weight of sample | m | (−0.5 g) |
| Extinction coefficient E % | 2500 | cm$^{-1}$%$^{-1}$ |
| Injected concentration (mg/l) | I | (−4) |

$I = Abs \times 25 \times 10,000/(2,500 \times 10) = Abs \times 10$

II—Calculation for Determination of Cis and Trans Percentages

| Peak area of all-trans beta-carotene | T | (17%) R.T.- 13.6 minutes |
|---|---|---|
| Peak area of unknown cis isomer 1 | C1 | R.T.- 14 minutes (not seen in above chromatogram) |
| Peak area of unknown cis isomer 2 | C2 | (9.8%) R.T.- 14.7 minutes |
| Peak area of 9-cis isomer | C3 | (43%) R.T.- 15.5 minutes |
| Peak area of 15-cis Isomer | C4 | (8%) R.T.- 16.68 minutes |

The retention times used in the above table are the retention times that were seen in the chromatogram shown in FIG. 1. In the chromatogram shown in FIG. 1, a peak was not seen for unknown cis isomer 1 ("the C1 peak"). Typically, this isomer will be seen after a retention time of about 14 minutes. The percentages given in the above table are approximate.

The individual peak areas are determined as a percentage by dividing the individual peak areas by the total peak area and multiplying the result by 100 to give the percentage of total carotenoid. These percentages appear under the heading "Conc" in the table that appears below the example chromatogram in FIG. 1.

Alternatively, the following formula can also be used in calculating the cis isomers percentage of the total carotenoid content. The formula presumes that a C1 peak is seen in the chromatogram:

$$\text{Cis \%} = (C1+C2+C3+C4/(\text{Total peak areas})) \times 100\%$$

Cis isomers are not always fully resolved but this does not effect their total cis isomer absorbance. In this regard, the C1 peak is not always fully resolved or separated from the other cis isomers. In this case, the C1 peak can be neglected from the calculation.

The all trans isomer percentage of the carotenoid content can also be determined by the following formula:

$$\text{Trans \%} = (T/(\text{Total peak areas})) \times 100\%$$

When conducting this type of analysis it is recommended that low actinic glasswater is used as beta-carotene is degraded slowly in light. The analysis should also be performed in duplicate because the retention times are very dependant on temperature, the column and solvents should be maintained at 20° C.

Accordingly, the invention provides a novel carotenoid composition derived from a natural source, of high cis beta-carotene content.

I claim:

1. A carotenoid composition derived from a natural source, wherein at least 50% by weight of the carotenoid content of the composition is cis beta-carotene.

2. A carotenoid composition according to claim 1, wherein the cis beta-carotene content of the composition is between at least 50% and 80% by weight.

3. A carotenoid composition according to claim 1, wherein the cis beta-carotene content of the composition is between 60% and 70% by weight.

4. A carotenoid composition according to claim 1, wherein the cis beta-carotene content of the composition is between 60% and 85% by weight.

5. A carotenoid composition according to claim 1, wherein the composition is predominantly 9 cis beta-carotene.

6. A carotenoid composition according to claim 1, wherein the composition comprises 70% 9 cis beta-carotene by weight.

7. A carotenoid composition according to claim 5 wherein the source of the 9 cis beta-carotene is selected from the group consisting of plant products, flowers of certain species of the Acacia genus, *cucurbitaceae* and *Dunalliela salinea* and mixtures thereof.

8. A carotenoid composition according to claim 5, wherein the source of the 9 cis beta-carotene is *Dunaliella salina*.

9. A carotenoid composition according to claim 1, wherein the composition is dispersed in a natural carrier oil selected from the group consisting of animal oil, vegetable oil, and mineral oil, and mixtures thereof.

10. A carotenoid composition according to claim 9, wherein the oil carrier is selected from olive, corn, soya bean, essential oils, terpene based oils, fish derived oils and mixtures thereof.

11. A carotenoid composition according to claim 1, wherein the composition further comprises small quantities of oil soluble anti-oxidants in the range of 0.01% to 1.0% by weight of pure anti-oxidant.

12. A carotenoid composition according to claim 1, wherein the composition further comprises small quantities of oil soluble anti-oxidants in the range of 0.01% to 0.5% by weight of pure anti-oxidant.

13. A carotenoid composition according to claim 11, wherein the anti-oxidant is selected from butylated hydroxy anisole, butylated hydroxytoluene, propyl gallate, ethoxyquin and ascorbyl palmitate plus other internal antioxidant extracts which may be derived from herbs, and natural tocopherols, and mixtures thereof.

14. A method for producing a carotenoid composition derived from a natural source, wherein the carotenoid composition contains at least 50% by weight of cis-beta-carotene, said method comprising (a) forming a carotenoid-containing preparation from the natural source, (b) treating the preparation by using density differentiation means, so as to separate cis-isomer carotenoids from trans-isomer carotenoids contained in the preparation.

15. The method of claim 14, wherein the density differentiation means include centrifugation.

16. A method of producing a carotenoid composition derived from the group consisting of a natural source, wherein the carotenoid composition contains at least 50% by weight of cis-beta-carotene, said method comprising (a) forming a cartenoid-containing preparation from the natural source, (b) treating preparation by using the filtration means so as to separate cis-isomer carotenoids from trans-isomer carotenoids contained in the preparation.

17. The method of claim 16, wherein the filtration means is selected from the group consisting of a filter press, a drum filter, a filter bed, a filter cartridge system, a membrane filter or a combination of the foregoing.

18. A carotenoid composition according to claim 7, wherein the plant products are apricots.

19. A carotenoid composition according to claim 13, wherein the antioxidants are natural tocopherols.

* * * * *